United States Patent [19]

Huyffer

[11] 3,933,849

[45] Jan. 20, 1976

[54] 3,3-DISUBSTITUTED PHTHALIDES AND NAPHTHALIDES

[75] Inventor: Paul S. Huyffer, West Boxford, Mass.

[73] Assignee: Polaroid Corporation, Cambridge, Mass.

[22] Filed: Apr. 26, 1974

[21] Appl. No.: 464,995

Related U.S. Application Data

[63] Continuation-in-part of Ser. No. 202,555, Nov. 26, 1971, Pat. No. 3,816,120.

[52] U.S. Cl. .................................................. 260/315

[51] Int. Cl.² ........................................ C07D 209/86

[58] Field of Search ..................................... 260/315

[56] References Cited

UNITED STATES PATENTS

| | | | |
|---|---|---|---|
| 3,491,111 | 1/1970 | Lin | 260/315 |
| 3,647,437 | 3/1972 | Land | 96/84 R |
| 3,702,244 | 11/1972 | Bloom et al. | 96/3 |

*Primary Examiner*—Sherman D. Winters
*Attorney, Agent, or Firm*—Sybil A. Campbell

[57] ABSTRACT

This invention relates to a class of phthalein indicator dyes useful as optical filter agents in photographic processes to protect a selectively exposed photosensitive material from further exposure during processing in the presence of incident light. Such dyes comprise 3,3-disubstituted phthalides and 3,3-disubstituted naphthalides wherein one of said 3,3 substituents is a carbazol-3-yl radical and the other is an indol-3-yl radical possessing a hydrogen-bonding group substituted on a carbon atom adjacent to the heterocyclic N atom, both of said carbazolyl and indolyl radicals having hydrogen substituted on the heterocyclic N atom.

19 Claims, No Drawings

3,3-DISUBSTITUTED PHTHALIDES AND NAPHTHALIDES

CROSS-REFERENCE TO RELATED APPLICATIONS

This application is a continuation-in-part of my copending application Ser. No. 202,555 filed Nov. 26, 1971, now U.S. Pat. No. 3,816,120.

BACKGROUND OF THE INVENTION

1. Field of the Invention

The present invention relates to novel chemical compounds and, more specifically, it relates to a new class of phthalein indicator dyes and to a method for the preparation thereof. In a particular aspect it relates to certain indole phthaleins useful as optical filter agents in photographic processes for protecting an exposed photosensitive material from post-exposure fogging during development in the presence of extraneous incident light.

2. Description of the Prior Art

A number of photographic processes by which images may be developed and viewed within seconds or minutes after exposure have been proposed. Such processes generally employ a processing composition which is suitably distributed between two sheet-like elements, the desired image being carried by one of said sheet-like elements. The resulting images may be in black-and-white, e.g., in silver, or in one or more colors. Processing may be conducted in or outside of a camera. The most useful of such processes are the diffusion transfer processes which have been proposed for forming silver or dye images, and several of these processes have been commercialized. Such processes have in common the feature that the final image is a function of the formation of an image-wise distribution of an image-providing reagent and the diffusion transfer of said distribution to or from the stratum carrying the final image, whether positive or negative.

U.S. Pat. No. 3,415,644 dicloses a composite photosensitive structure, particularly adapted for use in reflection type photographic diffusion transfer color processes. This structure comprises a plurality of essential layers including, in sequence, a dimensionally stable opaque layer; one or more silver halide emulsion layers having associated therewith dye image-providing material which is soluble and diffusible, in alkali, at a first pH, as a function of the point-to-point degree of its associated silver halide emulsion's exposure to incident actinic radiation; a polymeric layer adapted to receive solubilized dye image-providing material diffusing thereto; a polymeric layer containing sufficient acidifying capacity to effect reduction of a processing composition from the first pH to a second pH at which the dye image-providing material is substantially nondiffusible; and a dimensionally stable transparent layer. This structure may be exposed to incident actinic radiation and processed by interposing, intermediate the silver halide emulsion layer and the reception layer, an alkaline processing composition providing the first pH and containing a light-reflecting agent, for example, titanium dioxide to provide a white background. The light reflecting agent (referred to in said patent as an "opacifying agent") also performs an opacifying function, i.e., it is effective to mask the developed silver halide emulsions and also acts to protect the photoexposed emulsions from postexposure fogging by light passing through the transparent layer if the photoexposed film unit is removed from the camera before image formation is complete.

In a preferred embodiment, the composite photosensitive structure includes a rupturable container, retaining the alkaline processing composition having the first pH and light-reflecting agent, fixedly positioned extending transverse a leading edge of the composite structure in order to effect, upon application of compressive pressure to the container, discharge of the processing composition intermediate the opposed surfaces of the reception layer and the next adjacent silver halide emulsion.

The liquid processing composition distributed intermediate the reception layer and the silver halide emulsion, permeates the silver halide emulsion layers of the composite photosensitive structure to initiate development of the latent images contained therein resultant from photoexposure. As a consequence of the development of the latent images, dye image-providing material associated with each of the respective silver halide emulsion layers is individually immobilized as a function of the point-to-point degree of the respective silver halide emulsion layer photoexposure, resulting in imagewise distributions of mobile dye image-providing materials adapted to transfer, by diffusion, to the reception layer to provide the desired transfer dye image. Subsequent to substantial dye image formation in the reception layer, a sufficient portion of the ions of the alkaline processing composition transfers, by diffusion, to the polymeric neutralizing layer to effect reduction in the alkalinity of the composite film unit to the second pH at which dye image-providing material is substantially nondiffusible, and further dye image-providing material transfer is thereby substantially obviated.

The transfer dye image is viewed, as a reflection image, through the dimensionally stable transparent layer against the background provided by the reflecting agent, distributed as a component of the processing composition, intermediate the reception layer and next adjacent silver halide emulsion layer. The thus-formed stratum effectively masks residual dye image-providing material retained in association with the developed silver halide emulsion layer subsequent to processing.

In the copending U.S. Patent Application Ser. No. 786,352 of Edwin H. Land, filed Dec. 23, 1968, now abandoned, and Ser. No. 101,968 filed Dec. 28, 1970, now U.S. Pat. No. 3,647,437, in part a continuation of Ser. No. 786,352, an organic light absorbing reagent (or optical filter agent), such as a dye, which is present as a light-absorbing species at the first pH and which may be converted to a substantially non-light-absorbing species at the second pH is used in conjunction with the light-reflecting agent to protect the selectively exposed silver halide emulsions from post-exposure fogging when development of the photoexposed emulsions is conducted in the presence of extraneous incident actinic radiation impinging on the transparent layer of the film unit.

In copending U.S. Patent Application Ser. No. 108,260 filed Jan. 21, 1971, now U.S. Pat. No. 3,702,244, pH-sensitive dyes which contain at least one indole radical bonded by the 2- or 3-position to a ring-closing moiety are disclosed as useful as optical filter agents for absorbing incident radiation actinic to selectively exposed photosensitive materials within a predetermined wavelength range in the shorter wavelength region of the visible spectrum. Among the dyes disclosed therein are indole phthaleins wherein at least one of the indole radicals is substituted with a hydrogen-bonding group capable of raising the pKa. Preferably, both indole radicals are substituted, for example, with hydrogen-bonding groups to obtain dyes having a pKa of 11 or more. These phthalein dyes form the subject matter of copending U.S. Patent Application Ser. No. 409,012 filed Nov. 23, 1973, a continuation-in-part of U.S. Pat. Application Ser. No. 108,277 filed Jan. 21, 1971, now abandoned.

The present invention is concerned with other high pKa indicator dyes disclosed in aforementioned copending application Ser. No. 108,260, now U.S. Pat. No. 3,702,244. These dyes comprise mixed phthalein indicators derived from indole and a second N-heterocyclic aryl compound.

SUMMARY OF THE INVENTION

It is, therefore, the primary object of the present invention to provide a novel class of phthalein indicator dyes.

It is another object of the present invention to provide a novel class of phthalein indicator dyes useful as optical filter agents in photographic processes for preventing post-exposure fogging of a selectively exposed photosensitive material during development in the presence of incident light.

It is a further object of the present invention to provide products, compositions and processes for the development of photosensitive materials in which the novel phthalein indicator dyes are used.

It is yet a further object of the present invention to provide novel indicator dye intermediates and a method for the preparation thereof.

Other objects of this invention will in part be obvious and will in part appear hereinafter.

The invention accordingly comprises the processes involving the several steps and the relation and order of one or more of such steps with respect to each of the others, and the products and compositions possessing the features, properties and the relation of elements which are exemplified in the following detailed disclosure, and the scope of the application of which will be indicated in the claims.

According to the present invention, there is provided a novel class of phthalein indicator dyes which contain an indole radical possessing a hydrogen-bonding group substituted on a carbon atom adjacent to the nitrogen atom of said radical, a carbazole radical and a ring-closing moiety selected from a phthalide and a naphthalide. These indicator dyes will be defined with greater particularity hereinafter.

Like phthalein dyes, generally, the dyes of the present invention exhibit reversibly alterable spectral absorption characteristics in response to changes in environmental pH. They have a colored, light-absorbing form in alkaline media at a first pH value above their pKa and a substantially colorless form, i.e., a form which is substantially non-light-absorbing in the visible spectrum at a second pH below their pKa. By pKa is meant the pH at which about 50% of the dye is present in its light-absorbing form and about 50% is present in its non-light-absorbing form.

It will be appreciated that such compounds will find utility in titrations and other analytical procedures where phthalein indicator dyes are commonly employed, for example, to measure changes in pH value as reflected by the change in color of the dye form one color to another or from colored to colorless or vice versa. The indicator dyes of the present invention, however, due to their pKa and spectral absorption characteristics are especially useful as optical filter agents in photographic processes where development of a selectively exposed photosensitive material is performed at least in part outside the confines of a camera in the presence of extraneous incident actinic radiation.

For a fuller understanding of the nature and objects of the invention, reference should be had to the following detailed description.

DESCRIPTION OF THE PREFERRED EMBODIMENTS

According to the present invention, it has been found that mixed phthalein indicator dyes which contain a carbazole radical and an indole radical substituted with a hydrogen-bonding group possess comparatively high pKa's of greater than 11. Their pKa characteristics together with their ability to absorb radiation in the shorter wavelength region of the visible spectrum and in the UV render them particularly useful as optical filter agents in photographic processes conducted under highly alkaline conditions. For example, such dyes find particular utility in diffusion transfer photographic processes since the dye will be in a light-absorbing form during the initial stages of processing and yet it may be rendered substantially non-light absorbing within a relatively brief interval as the pH is reduced subsequent to substantial image formation to permit early viewing of the image.

The novel indicator dyes of the present invention may be defined as 3,3-disubstituted phthalides and 3,3-disubstituted naphthalides wherein one of the 3,3 substituents is a carbazol-3-yl radical and the other is an indol-3-yl radical possessing a hydrogen-bonding group substituted on a carbon atom adjacent to the heterocyclic nitrogen atom, both of said carbazole and indole radicals having hydrogen substituted on the heterocyclic nitrogen atom. Typical of the indicator dyes of the present invention are those represented by the formula:

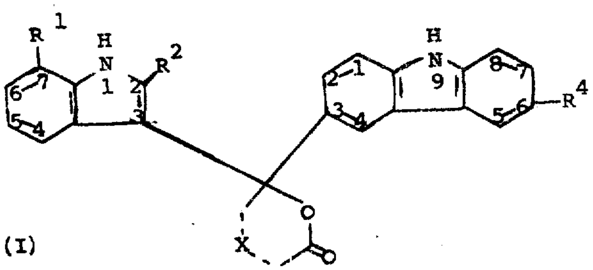

(I)

wherein one of $R^1$ and $R^2$ is a hydrogen-bonding group and the other is hydrogen, $R^4$ is hydrogen or a monovalent organic radical and X represents the atoms necessary to complete a ring-closing moiety selected from a phthalide and a naphthalide.

In the above formula, any hydrogen-bonding group may be used that is capable of raising the pKa. The association of two atoms through hydrogen to form a hydrogen bond between or within molecules is well known. When hydrogen is attached to an electronegative atom, for example, O or N, the resultant bond is polarized. If directed toward another atom (M) with an unshared pair of electrons, the hydrogen acts as a bridge between the atoms (O—H . . . M) due to the electrostatic attraction to both atoms between which the hydrogen proton can be transferred. In the above compounds, an intramolecular hydrogen bond is formed between the —NH— of the indole ring and an adjacent hydrogen-bonding group, i.e., a group containing a heteroatom possessing an active unshared pair of electrons, such as, O, N, S or halogen, e.g., F., which has a free electron pair or a negative charge in basic solution and which is capable of forming a 5-, 6- or 7-membered and preferably a 5- or 6-membered hydrogen-bonded ring with the —NH— of the indole ring. Groups containing a free electron pair include, for example, alkoxy; acyl and its derivatives

wherein R may be hydrogen, alkyl, aryl, aralkyl, alkaryl); and amido

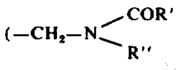

wherein R' and R'' each may be alkyl, aryl, aralkyl, alkaryl). Preferably, the heteroatom in the hydrogen-bonding group has attached to it a proton which is more acidic than the proton on the —NH— of the indole and ionizes in basic solution to a negative charge. Such groups include, for example, carboxy; hydroxy; o-hydroxyphenyl; bis trifluoromethyl carbinol; sulfonamide ($—NH—SO_2—R'''$ wherein R''' may be alkyl, aryl, aralkyl, alkaryl) and sulfamoyl ($—SO_2—NH—R''''$ wherein R'''' may be alkyl, aryl, aralkyl, alkaryl). Suitable R, R', R'', R''' and R'''' substituents include branched or straight chain alkyl, e.g., methyl, ethyl, isopropyl, n-butyl, t-butyl, hexyl, octyl, dodecyl, hexadecyl, octadecyl and eicosanyl; aryl, particularly phenyl and naphthyl; aralkyl and alkaryl, particularly phenyl-substituted alkyl and alkyl-substituted phenyl, e.g., benzyl, phenethyl, phenylhexyl, p-octylphenyl and p-dodecylphenyl. Though the hydrogen-bonding groups $R^1$ and $R^2$ may be any of those enumerated above, preferably they are among those having a negative charge in basic solution, particularly, carboxy, hydroxy, ortho-hydroxyphenyl, bis trifluoromethyl carbinol, sulfonamido and sulfamoyl.

In the above formula, the indole radical and/or carbazole radical and/or the ring-closing moiety may be substituted, for example, with solubilizing groups to enhance the solubility of the indicator dye in the particular processing composition employed; with immobilizing groups where it is desired to render the indicator dye substantially non-diffusible in the processing composition and with other substituents, such as alkyl groups, which do not interfere with the photographic function of the indicator dye as an optical filter agent.

Typical substituents include branched or straight chain alkyl, such as methyl, ethyl, isopropyl, n-butyl, t-butyl, hexyl, octyl, dodecyl, hexadecyl, octadecyl and eicosanyl; aryl, such as, phenyl, 2-hydroxyphenyl, 2-hydroxy-4-dodecyloxyphenyl, and naphthyl; aralkyl and alkaryl, such as, benzyl, phenethyl, phenylhexyl, p-octylphenyl, p-dodecyl-phenyl; alkoxy, such as, methoxy, ethoxy, butoxy, 1-ethoxy-2-($\beta$-ethoxyethoxy), dodecyloxy and octadecyloxy; aryloxy, such as phenoxy, benzyloxy, naphthoxy; alkoxyalkyl, such as methoxyethyl, dodecyloxyethyl; halo such as, fluoro, bromo, and chloro; trifluoroalkyl, such as trifluoromethyl; sulfonyl; sulfo; cyano; amino including mono- and disubstituted amino, e.g., N-ethyl amino and N, N'-dimethylamino, carboxy; and hydroxy.

In a preferred embodiment, the indicator dyes of the present invention comprise compounds of formula I above, wherein one of $R^1$ and $R^2$ is hydrogen and the other is a hydrogen-bonding group forming a 5-, 6- or 7-membered intramolecular hydrogen-bonded ring with the adjacent —NH— of the indole ring selected from carboxy, hydroxy, o-hydroxyphenyl, bis trifluoromethyl carbinol, sulfonamido and sulfamoyl; $R^4$ is hydrogen or alkyl containing 1 to 20 carbon atoms; and X represents the atoms necessary to complete a ring-closing moiety selected from phthalide and naphthalide.

Where it is desired that the indicator dye be substantially immobile or non-diffusible in the processing solution, compounds containing a sulfamoyl or sulfonamido substituent afford the distinct advantage of allowing the immobilizing function to be combined with the hydrogen bonding function by selecting sulfonamide or sulfamoyl groups containing as R''' or R'''' a substituent such as, hexadecyl or p-dodecylphenyl.

Specific examples of indicator dyes within the scope of the present invention are as follows:

(1)

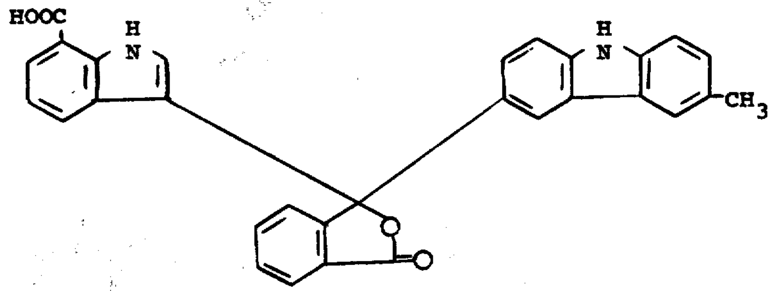

(2)

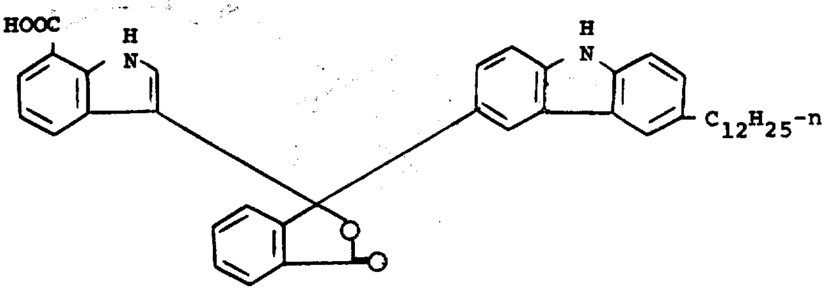

(3)
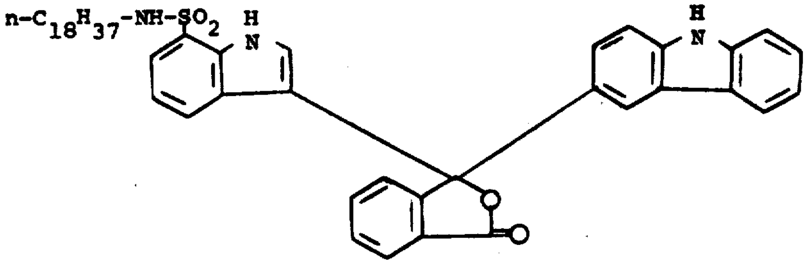
(4)
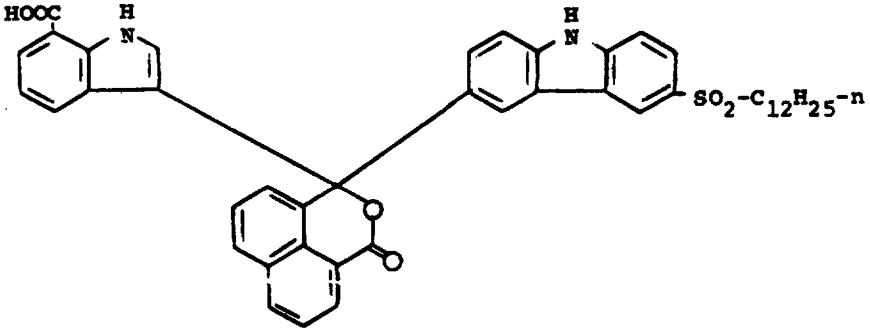
(5)
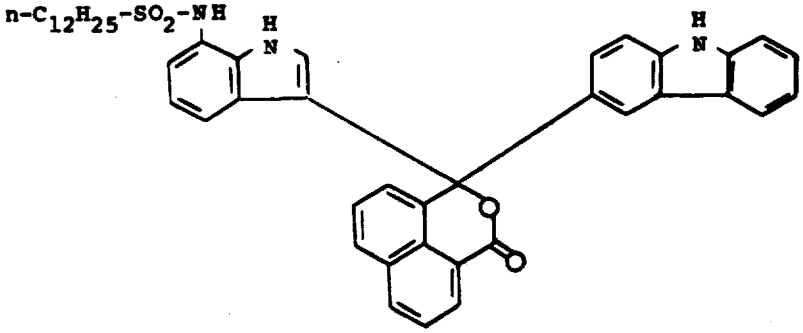
(6)
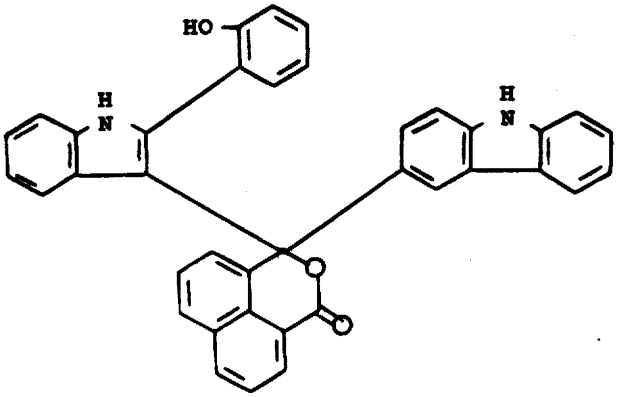
(7)
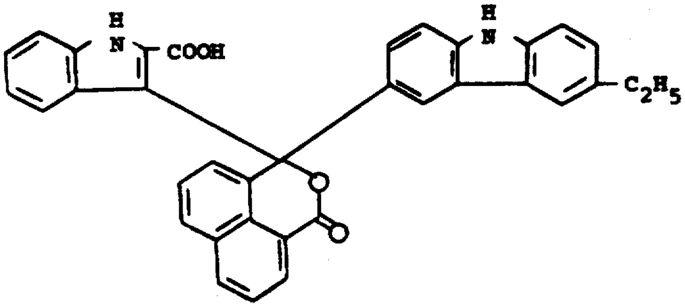

(8)
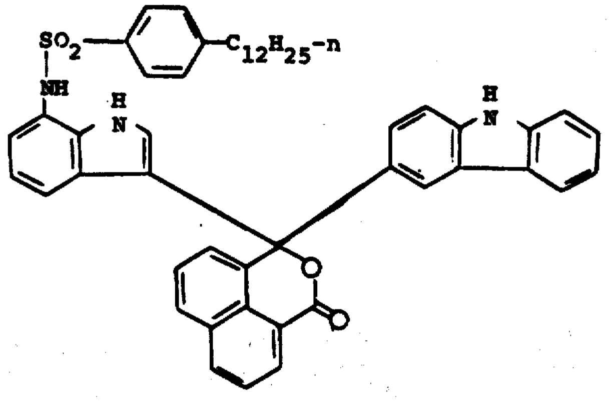
(9)
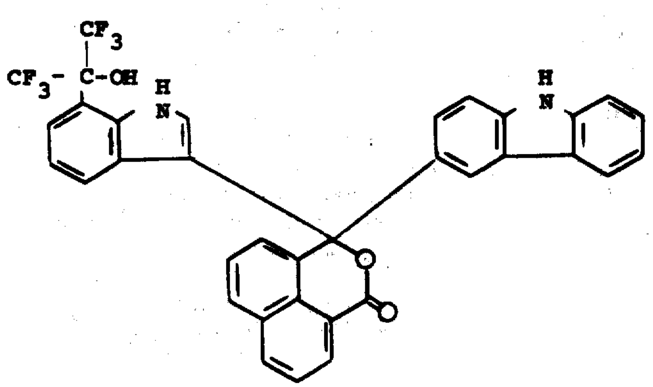
(10)
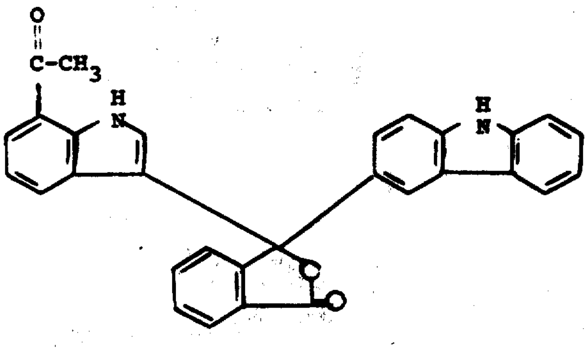
(11)
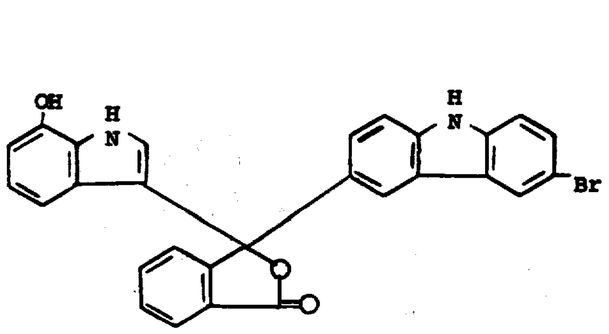

(12)

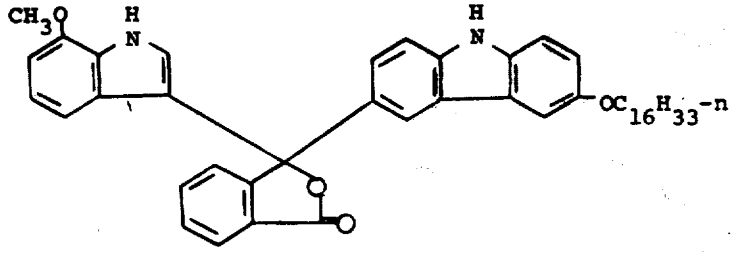

The indicator dyes of the present invention preferably are prepared utilizing novel intermediates comprising 3-aroyl 9-cyanoethylcarbazoles which preferably are substituted in the 6-position with a monovalent organic radical. Though carbazoles containing an alkyl substituent in the 9-position, for example, 9-ethylcarbazole have been employed in the synthesis of phthalein dyes, the use of these prior intermediates results in a mixture of reaction products making it difficult to isolate the desired product from the by-products. According to the present invention, it has been found that carbazoles containing a cyanoethyl group substituted on the heterocyclic nitrogen atom may be used in the production of phthaleins without any substantial formation of by-products particularly where the intermediate contains an organic radical as a blocking group in the 6-position of the carbazole ring.

The novel intermediates of the present invention may be represented by the following formula:

(II)

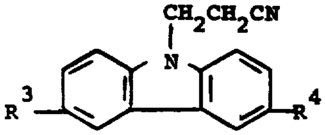

wherein $R^3$ is a group selected from 2-carboxybenzoyl and 8-carboxynaphthoyl and $R^4$ is a group selected from hydrogen and a monovalent organic radical.

As the $R^4$ substituent, any monovalent organic radical may be employed, for example, alkyl, such as, methyl, ethyl, butyl, hexyl, dodecyl, hexadecyl; alkenyl; such as, vinyl, alkyl, propenyl; cycloalkyl, such as, cyclobutyl, cyclohexyl, cycloheptyl, cyclopentyl; cycloalkenyl, such as, cyclohexenyl, cyclooctenyl, cyclopentenyl; aryl, such as, phenyl, naphthyl; alkaryl, such as, phenethyl, benzyl, p-dodecylphenyl; aryloxy, such as, phenoxy, naphthoxy, benzoxy; alkoxy, such as, butoxy, heptoxy, dodecyloxy, hexadecyloxy; halo, such as, chloro, bromo; nitro; carboxy; cyano; hydroxy; sulfonyl, acyl, and amino including mono- and di-substituted amino. Preferably, $R^4$ is hydrogen or alkyl containing 1 to 20 carbon atoms. The intermediates also may contain substituents other than those specified as may be desired in the indicator dye product.

Specific intermediates within the scope of the present invention include:

(13)

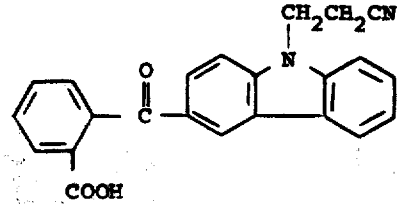

(14)

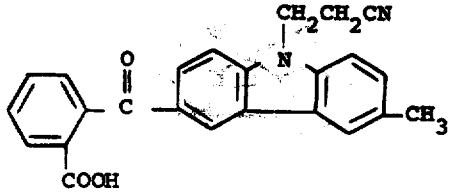

(15)

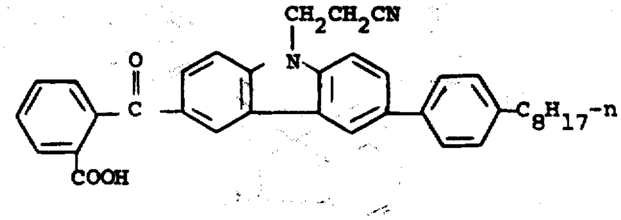

The novel carbazole intermediates represented above are prepared by reacting the selected $R^4$-substituted carbazole with acrylonitrile in the presence of a catalytic amount of strong base, e.g., benzyl trimethyl ammonium hydroxide at a temperature of about 80° to 120° C. to form the corresponding 9-cyanoethylcarbazole. The latter compound is reacted with phthalic or naphthalic acid or their anhydrides in inert media, preferably an aromatic hydrocarbon solvent in the presence of a suitable acid catalyst, such as zinc chloride, aluminum chloride or other Lewis acid catalyst at a temperature between about 0° and 50° C. to form the corresponding $R^3$- and $R^4$-disubstituted 9-cyanoethylcarbazole dye intermediate.

The indicator dyes are prepared by reacting the latter intermediate with the selected indole in the presence of a condensing agent, preferably, acetic anhydride. Where it is desired to remove the cyanoethyl group, the 9-cyanoethyl carbazole dye intermediate may be treated with strong base prior to reaction with the indole. Alternatively, the cyanoethyl group may be removed subsequent to reaction with the indole by treating the indicator dye product with strong base and then neutralizing. Particularly useful bases are alkali metal alkoxides, e.g., butoxide, sodium methoxide in inert organic media, particularly aprotic solvents, such as dimethylsulfoxide, N,N'-dimethylformamide and N,N'-diethylformamide.

As noted above, the carbazole intermediates of the present invention preferably contain a substituent in the 6-position. By using this blocking group together with the 9-cyanoethyl substituent, the formation of a single reaction product rather than a mixture of products is ensured. The 6-substituent also may be removed, if desired. For example, a halo group, such as, —Br may be removed by hydrogenation or a —COOH group by decarboxylation. It will also be appreciated that the subject intermediates may be employed in the production of phthalein indicator dyes containing a phenol, naphthol or other radical rather than indole as the second chromophoric radical.

The preparation of the novel intermediates of the present invention and the preparation of mixed carbazole/indole phthaleins therefrom is illustrated in the following reaction sequence.

(1)

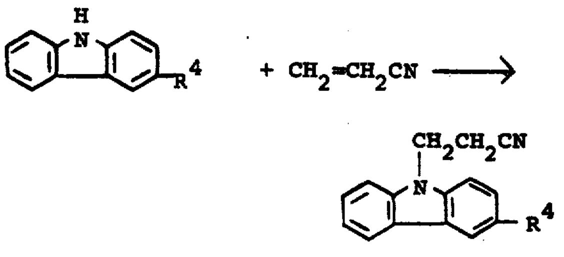

(2)

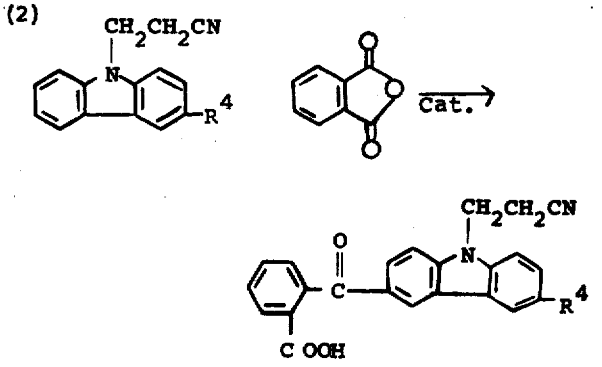

(3)

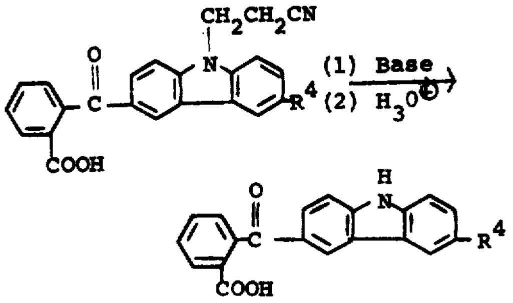

(4)

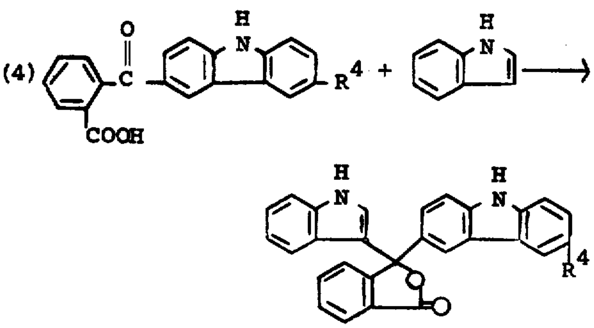

As discussed above, steps (3) and (4) in the foregoing reaction sequence may be reversed, that is, the indole may be reacted with the intermediate prior to removing the cyanoethyl group which may be subsequently removed from the indicator dye product by treatment with base.

The following Example is given to further illustrate the present invention and is not intended to limit the scope thereof.

EXAMPLE

Preparation of the indicator dye of formula (1):

a. The compound 6-methyl-9-cyanoethylcarbazole was prepared by stirring 6-methylcarbazole (0.05 mole) in acrylonitrile (0.20 mole) at 0°C. After adding about 1 cc. of benzyl trimethyl ammonium hydroxide, the mixture was stirred on a steam bath for one hour and then treated with boiling benzene (200 cc.). The benzene was distilled and evaporated to dryness. The yellow solid obtained was recrystallized from benzene with Norit treatment to yield 6-methyl-9-cyanoethylcarbazole as an off-white solid, melting range 124°-124.5°C.

b. A mixture of the compound prepared in step (a) (0.03 mole), phthalic anhydride (0.03 mole) and 50 ml. of benzene were stirred in an ice bath. Aluminum chloride (0.065 mole) was slowly added to the mixture, and after addition, the mixture was stirred for 30 minutes at 0°C. and then warmed to 50°C. and stirred for 3 hours. After cooling, 3N hydrochloric acid was added to decompose the aluminum complex. The yellow solid that formed was filtered and stirred in warm dilute ammonium hydroxide. The hydroxide solution was filtered, and the filtrate was neutralized with dilute hydrochloric acid. The solid obtained upon neutralization was recrystallized from xylene to give 3-(o-carboxybenzoyl)-6-methyl-9-cyanoethylcarbazole as white crystals, melting point 190°C.

c. The o-carboxybenzoyl carbazole intermediate prepared in step (b) (14 gms.) together with potassium-t-butoxide (14 gms.) were heated in 100 ml. of dimethylsulfoxide on a steam bath for 2 hours and precipitated into water which gave a clear red solution. Acidification of the solution with hydrochloric acid gave a pinkish precipitate which was collected and dissolved in warm acetic acid. Norit and Celite were added to the solution and the solution was filtered. Hot water (about 2 volumes) was added to the filtrate until crystallization of the 3-(o-carboxybenzoyl)-6-methylcarbazole which was recovered as a light yellow solid, melting range 261°–262°C. (dec.).

d. 7-carboxyindole (0.0015 m.) and 6-methyl-3-(ortho-carboxybenzoyl)carbazole (0.0015 m.) were refluxed in acetic anhydride for about one-half hour, and the reaction mixture precipitated into water. After standing overnight, the water was decanted, leaving the precipitate which was washed with water followed by extraction with aqueous ammonium hydroxide solution. Upon acidification of the ammonium hydroxide solution, the title compound was obtained as a white solid which gave a purple color in 20% aqueous sodium hydroxide solution.

It will be appreciated that other carbazoles and other indoles, for example, 7-sulfonamidoindoles and 7-sulfamoylindoles may be substituted in the procedure of the foregoing example and that phthalic or naphthalic acid or naphthalic anhydride may be used instead of phthalic anhydride. Also, other Lewis acid catalysts, solvents and bases may be employed, such as those enumerated above.

As noted previously, the indicator dyes of the present invention possess a relatively high pKa. The pKa value measured for the dye prepared in the Example was 13.2 which is in the same range as the values for the indole phthaleins of aforementioned application Ser. No. 108,277 which contain two indol-3-yl radicals each substituted with a hydrogen-bonding group. As a comparison, 3,3-di-(2-ortho-hydroxyphenyl indol-3-yl)phthalide has a pKa of 13.4 and 3-(7-carboxy-indol-3-yl)-3-(2-ortho-hydroxyphenyl indol-3-yl)phthalide has a pKa of 13.3. As a further comparison, a simple indole phthalein, i.e., without a hydrogen-bonding group, such as, 3,3-di(2-phenylindol-3-yl) phthalide has a lower pKa of 9.0. From these values, it can be seen that the mixed indole phthaleins of the present invention, like the indole phthaleins possessing hydrogen-bonding substituents, may be rendered colorless at a high pH and thus, cleared more rapidly than simple indole phthaleins in photographic processes conducted in highly alkaline media.

Another class of indicator dyes derived from carbazoles forms the subject matter of copending U.S. Patent Application Ser. No. 202,482 of Ruth C. Bilofsky and Richard D. Cramer filed Nov. 26, 1971. Such dyes comprise 3,6-disubstituted carbazoles wherein the 3,6 substituents are selected from a phthalidyl radical, $$C_6H_4.CO.O.CR-,$$

wherein R is an aryl group and an o-carboxybenzoyl radical, not more than one of said substituents being o-carboxybenzoyl.

The pH sensitive indicator dyes of the present invention may be used as optical filter agents in any photographic process including conventional tray processing and diffusion transfer photographic techniques. In such processes, the dye or dyes during development of a selectively exposed photosensitive material will be in a position and in a concentration effective to absorb a given level of non-selective radiation incident on and actinic to the photosensitive material. The dyes may be initially disposed in the film unit, for example, in a layer(s) coextensive with one or both surfaces of the photosensitive layer. Where selective exposure of the photosensitive material is made through a layer containing the indicator dye, then the dyes should be in a non-light-absorbing form until the processing solution is applied. Alternately, the dyes may be initially disposed in the processing composition in their light-absorbing form, for example, in the developing bath in tray processing or in the layer of processing solution distributed between the photosensitive element and the superposed image-receiving element (or spreader sheet) in diffusion transfer processing. The particular indicator dye or dyes selected should have an absorption spectrum corresponding to the sensitivity of the photosensitive layer, so as to afford protection over the predetermined wavelength range required by the particular photosensitive material employed and should have a pka such that they are in their colored form, i.e., light-absorbing form at the pH at which the photographic process is performed. Most commercially useful photographic processes are performed under alkaline conditions. Diffusion transfer processes, for example, usually employ highly alkaline processing solutions having a pH in excess of 12.

In photographic processes where the optical filter agent is retained in a stratum through which the final image is to be viewed, the color of the indicator dye may be discharged subsequent to image formation by adjusting the pH of the system to a value at which the dye is substantially non-light absorbing in the visible spectrum. In photographic processes performed at an alkaline pH, the optical filter agent, such as, a dye or dyes of the present invention are rendered substantially colorless by reducing the environmental pH. In processes where the optical filter agent is removed or separated from the layer containing the final image or retained in a layer that does not interfere with viewing of the final image, it is unnecessary to convert the indicator dye to its non-light-absorbing form, though the color may be discharged if desired.

The concentration of indicator dye is selected to provide the optical transmission density required, in combination with other layers intermediate the silver halide emulsion layer(s) and the incident radiation, to prevent nonimagewise exposure, i.e., fogging, by incident actinic light during the performance of the particular photographic process. It has been found, by interposing neutral density (carbon containing) filters over a layer of titanium dioxide, that a transmission density of approximately 6.0 from said neutral density filters was effective to prevent fogging of a diffusion transfer multicolor film unit of the type described in said U.S. Pat. No. 3,415,644 having a transparent support layer and an Equivalent ASA Exposure Index of approximately 75, when processed for one minute in 10,000 foot candles of color corrected light, a light intensity approximating the intensity of a noon summer sun. The transmission density required to protect such a film unit under the stated conditions may also be expressed in terms of the "system" transmission density of all the layers intermediate the silver halide layer(s) and the incident light; the "system" transmission density required to protect color film units of the aforementioned type and photographic speed has been found to be on the order of 7.0 to 7.2. Lesser levels of optical transmission density would, of course, provide effective protection for shorter processing times, lesser light intensities and/or films having lower exposure indices. The transmission density and the indicator dye concentration necessary to provide the requisite protection from incident light may be readily determined for any photographic process by following the above described procedure or obvious modifications thereof.

Since most commercial photographic processes employ photosensitive materials sensitive to and exposable by actinic radiation throughout the visible spectrum, e.g., black-and-white panchromatic silver halide emulsions and multilayer silver halide emulsion elements, it is preferred to use a second dye(s) in conjunction with the subject dye(s) that has a principal absorption in a second and at least partially different predetermined wavelength range such that the combination of dyes will afford protection from non-selective incident actinic radiation over the range of 400 to 700 nm. The second dye employed may be non-color-changing but preferably, is also pH sensitive, i.e., has reversibly alterable spectral absorption characteristics in response to changes in the environmental pH so that it may be rendered light-absorbing or non-light-absorbing as desired. Illustrative of such dyes are phthaleins derived from phenols, such as, thymol phthalein. The second dye also may be initially present in the film unit or in the processing composition as discussed above either together with or separate from the subject dyes and subsequent to processing may be removed from the film unit or retained within the film structure, provided it is in a form or position such that it does not interfere with viewing of the image produced.

The dyes of the present invention are especially useful as optical filter agents in diffusion transfer processes, for example, those employing composite diffusion transfer photosensitive elements including a film pack or roll wherein superposed photosensitive and image-receiving elements are maintained as a laminate after formation of the final image. Such elements include at least one transparent support to allow viewing of the final image without destroying the structural integrity of the film unit. Preferably, the support carrying the photosensitive layer(s) is opaque and the support carrying the image-receiving layer is transparent and selective photoexposure of the photosensitive layer(s) and viewing of the final image both are effected through the latter support. The final image is viewed as a reflection print, i.e., by reflected light, provided by a reflecting agent initially disposed in the processing composition applied and maintained intermediate the image-receiving and next adjacent photosensitive layer or by a preformed layer of reflecting agent initially positioned intermediate the image-receiving and next adjacent photosensitive layer. It will be understood that a preformed reflecting layer, while it should be capable of masking the photosensitive layer(s) subsequent to image formation, should not interfere with selective photoexposure of the photosensitive material prior to processing.

When utilizing reflection-type composite film units, the indicator dye or dyes employed as the optical filter agent(s) may be positioned initially in a layer of the film unit, e.g., in a layer between the image-receiving and next adjacent photosensitive layer through which photo-exposure is effected provided it is incorporated under conditions, i.e., at a pH such that it will not absorb actinic radiation intended to selectively expose the photosensitive material to form a latent image therein. For example, the optical filter agent may be in a layer coated over either the image-receiving layer or the next adjacent photosensitive layer and should remain substantially non-light-absorbing until a processing composition is applied providing a pH at which the indicator dye is capable of being rapidly converted to its light-absorbing form to provide light protection when the film unit is removed from the camera. Rather than being initially disposed in the film unit, the indicator dye may be initially present in the processing composition applied intermediate the image-receiving and next adjacent photosensitive layer subsequent to photoexposure. The dye, when initially disposed in the processing composition, will be in its light-absorbing form.

The dyes selected as optical filter agents should exhibit at the initial pH of the processing, maximum spectral absorption of radiation at the wavelengths to which the film unit's photosensitive silver halide layer or layers are sensitive, and preferably, should be substantially immobile or non-diffusible in the alkaline processing composition in order to achieve optimum efficiency as a radiation filter and to prevent diffusion of filter agent into layers of the film unit where its presence may be undesirable. Recognizing that the filter agent absorption will detract from image-viewing characteristics by contaminating reflecting pigment background, the selected agents should be those exhibiting major spectral absorption at the pH at which processing is effected and minimal absorption at a pH below that which obtains during transfer image formation. Accordingly, the selected optical filter agent or agents should possess a pKa below that of the processing pH and above that of the environmental pH subsequent to transfer image formation.

As discussed previously, the concentration of indicator dye is selected to provide the optical transmission density required, in combination with other layers intermediate the silver halide emulsion layer(s) and the incident radiation, to prevent nonimagewise exposure, i.e., fogging, by incident actinic light during the performance of the particular photographic process. In the processes where the indicator dye or dyes selected as optical filter agents are used in conjunction with a reflecting agent or agents, the optical filter agents and reflecting agents together should possess the optical transmission density necessary to protect the photosensitive material for the particular photographic process. The optimum concentration of optical filter agent(s) or filter agent(s) together with reflecting agent(s) may be readily determined empirically for each photographic system.

While substantially any reflecting agent may be employed for the layer of reflecting agent, either preformed or applied as a component of the processing composition, it is preferred to select an agent that will not interfere with the color integrity of the dye transfer image, as viewed by the observer, and, most preferably, an agent which is aesthetically pleasing to the viewer and does not provide a background detracting from the information content of the image. Particularly desirable reflecting agents will be those providing a white background, for viewing the transfer image, and specifically those conventionally employed to provide background for reflection photographic prints and, especially, those agents possessing the optical properties desired for reflection of incident radiation.

As examples of reflecting agents, mention may be made of barium sulfate, zinc sulfide, titanium dioxide, barium stearate, silver flake, silicates, alumina, zirconium oxide, zirconium acetyl acetate, sodium zirconium sulfate, kaolin, mica, and the like.

Illustrative of the photographic use of the indicator dyes of the present invention as optical filter agents, a photographic film unit may be prepared by coating, in succession, on a gelatin subbed, 4 mil. opaque polyethylene terephthalate film base, the following layers:

1. a layer of the cyan dye developer 1,4-bis-($\beta$-[hydroquinonyl-$\alpha$-methyl]-ethylamino)-5,8-dihydroxyanthraquinone dispersed in gelatin and coated at a coverage of about 80 mgs./ft.$^2$ of dye and about 100 mgs./ft.$^2$ of gelatin;

2. A red-sensitive gelatino-silver iodobromide emulsion coated at a coverage of about 225 mgs./ft.$^2$ of silver and about 50 mgs./ft.$^2$ of gelatin;

3. a layer of the acrylic latex sold by Rohm and Haas Co., Philadelphia, Pennsylvania, U.S.A., under the trade designation AC-61 and polyacrylamide coated at a coverage of about 150 mgs./ft.$^2$ of AC-61 and about 5 mgs/ft.$^2$ of polyacrylamide;

4. a layer of the magenta dye developer 2-(p-[β-hydroquinonylethyl]-phenylazo)-4-isopropoxy-1-naphthol dispersed in gelatin and coated at a coverage of 70 mgs./ft.$^2$ of dye and about 120 mgs./ft.$^2$ of gelatin;

5. a green-sensitive gelatino-silver iodobromide emulsion coated at a coverage of about 120 mgs./ft.$^2$ of silver and 60 mgs./ft.$^2$ of gelatin;

6. a layer comprising the acrylic latex sold by Rohm and Haas Co. under the trade designation B-15 and polyacrylamide coated at a coverage of about 100 mgs./ft.$^2$ of B-15 and about 10 mgs./ft.$^2$ of polyacrylamide;

7. a layer of the yellow dye developer 4-(p-[β-hydroquinonylethyl]-phenylazo)-3-(N-n-hexyl-carboxamido)-1-phenyl-5-pyrazolone and the auxiliary developer 4'-methylphenyl hydroquinone dispersed in gelatin and coated at a coverage of about 50 mgs./ft.$^2$ of dye, about 15 mgs./ft.$^2$ of auxiliary developer and 50 mgs./ft.$^2$ of gelatin;

8. a blue-sensitive gelatino-silver iodobromide emulsion coated at a coverage of about 75 mgs./ft.$^2$ of silver and about 75 mgs./ft.$^2$ of gelatin; and 9. a layer of gelatin coated at a coverage of about 50 mgs./ft.$^2$ of gelatin.

Then a transparent 4 mil. polyethylene terephthalate film base may be coated, in succession, with the following illustrative layers:

1. a 7:3 mixture, by weight, of polyethylene/maleic acid copolymer and polyvinyl alcohol at a coverage of about 1400 mgs./ft.$^2$, to provide a polymeric acid layer;

2. a graft copolymer of acrylamide and diacetone acrylamide on a polyvinyl alcohol backbone in a molar ratio of 1:3.2:1 at a coverage of about 800 mgs./ft.$^2$, to provide a polymeric spacer layer; and 3. a 2:1 mixture, by weight, of polyvinyl alcohol and poly-4-vinylpyridine, at a coverage of about 900 mgs./ft.$^2$ and including about 20 mgs./ft.$^2$ phenyl mercapto tetrazole, to provide a polymeric image-receiving layer.

The two components thus prepared may then be taped together in laminate form, at their respective edges, by means of a pressure-sensitive binding tape extending around, in contact with, and over the edges of the resultant laminate.

A rupturable container comprising an outer layer of lead foil and an inner liner or layer of polyvinyl chloride retaining an aqueous alkaline processing solution comprising:

| | | |
|---|---|---|
| Water | 100 | cc. |
| Potassium hydroxide | 11.2 | gms. |
| Hydroxyethyl cellulose (high viscosity) [commercially available from Hercules Powder Co., Wilmington, Delaware, under the trade name Natrasol 250] | 3.4 | gms. |
| N-phenethyl-α-picolinium bromide | 2.7 | gms. |
| Benzotriazole | 1.15 | gms. |
| Titanium dioxide | 50.0 | gms. |

1.0 gm.

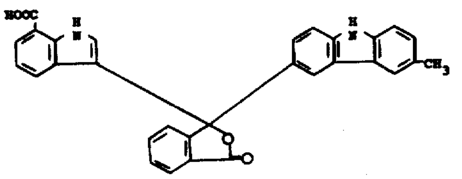

1.0 gm.

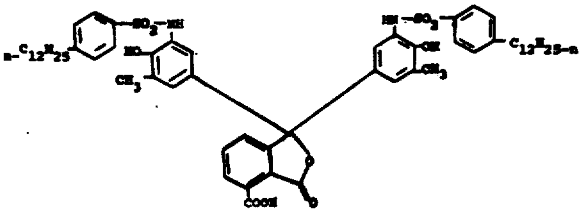

1.0 gm.

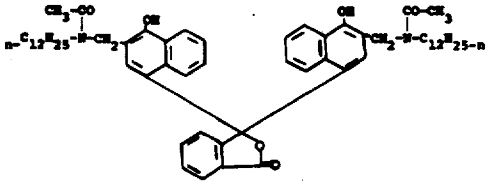

may then be fixedly mounted on the leading edge of each of the laminates, by pressure-sensitive tapes interconnecting the respective containers and laminates, such that, upon application of compressive pressure to a container, its contents may be distributed, upon rupture of the container's marginal seal, between the polymeric image-receiving layer and next adjacent gelatin layer.

The photosensitive composite film units may be exposed through step wedges to selectively filter radiation incident on the transparent polyethylene terephthalate layer and processed by passage of the exposed film units through appropriate pressure-applying members, such as suitably gapped, opposed rolls, to effect rupture of the container and distribution of its contents. During processing, the multicolor dye transfer image formation may be viewed through the transparent polyethylene terephthalate layer against the titanium dioxide background provided by distribution of the pigment containing processing composition between the polymeric image-receiving layer and gelatin layer 9 of the photosensitive component. The film unit may be exposed to incident light and the formation of the image may be viewed upon distribution of the processing composition by reason of the protection against incident radiation afforded the photosensitive silver halide emulsion layers by the optical filter agents and by reason of the effective reflective background afforded by the titanium dioxide.

The spectral absorption characteristics of the indicator dye prepared in the above Example graphically illustrated in FIG. 17 of the aforementioned copending Application Ser. No. 108,260 which graph represents the optical transmission density, i.e., absorbance of the dye measured on a logarithm scale over the wavelength range of 350 nm. to 750 nm. in aqueous alkaline solution at a pH substantially above its pKa.

The film unit detailed above is similar to that shown in FIG. 2 and related FIGS. 3 and 4 of aforementioned copending U.S. Patent Application Ser. No. 101,968. The negative component of the film unit including the photosensitive strata and associated dye-image-forming material; the positive component including the timing, neutralizing and dyeable layers; and the processing composition including its components, such as, the alkaline material and various addenda are described in detail in Application Ser. No. 101,968. For convenience, the specification of this application is specifically incorporated herein.

Besides the above photosensitive element, the dyes of the present invention may be employed in composite photosensitive elements, in general, where the dyeable stratum along with any associated layers may be contained together with the photosensitive strata as a unitary film which may be termed an integral negative-positive film unit comprising a negative component including the aforementioned essential layers and a positive component including at least the dyeable stratum in which the color transfer image is to be formed. The essential layers are preferably contained on a transparent dimensionally stable layer or support member positioned closest to the dyeable stratum so that the resulting transfer image is viewable through this transparent layer. Most preferably another dimensionally stable layer which may be transparent or opaque is positioned on the opposed surface of the essential layers so that the aforementioned essential layers are sandwiched or confined between a pair of dimensionally stable layers or support members, at least one of which is transparent to permit viewing therethrough of a color transfer image obtained as a function of development of the exposed film unit in accordance with the known color diffusion transfer processes. It will be appreciated that all of these film units, like the specific one detailed above, may optionally contain other layers performing specific desired functions, e.g., spacer layers, pH-reducing layers, etc.

Examples of such integral negative-positive film units for preparing color transfer images viewable without separation are those described and claimed in aforementioned U.S. Pat. No. 3,415,644 and in U.S. Pat. Nos. 3,415,645, 3,415,646, 3,473,925, and 3,573,043.

In general, the film units of the foregoing description, e.g., those described in the aforementioned patents and/or copending applications, are exposed to form a developable image and thereafter developed by applying the appropriate processing composition to develop exposed silver halide and to form, as a function of development, an imagewise distribution of diffusible dye image-providing material which is transferred, at least in part by diffusion, to the dyeable stratum to impart thereto the desired color transfer image, e.g., a positive color transfer image. Common to all of these systems is the provision of a reflecting layer between the dyeable stratum and the photosensitive strata to mask effectively the latter and to provide a background for viewing the color image contained in the dyeable stratum, whereby this image is viewable without separation, from the other layers or elements of the film unit. As discussed previously, in some embodiments this reflecting layer is provided prior to photoexposure, e.g., as a preformed layer included in the essential layers of the laminar structure comprising the film unit, and in others it is provided at some time thereafter, e.g., by including a suitable light-reflecting agent, for example, a white pigment, such as, titanium dioxide, in the processing composition. As an example of such a preformed layer, mention may be made of that disclosed in the copending applications of Edwin H. Land, Ser. Nos. 846,441, filed July 31, 1969, and 3,645, filed Jan. 19, 1970 and now U.S. Pat. Nos. 3,615,421 and 3,620,724. The reflecting pigment may be generated in situ as is disclosed in the copending applications of Edwin H. Land, Ser. Nos. 43,741 and 43,742, both filed June 5, 1970 and now U.S. Pat. Nos. 3,647,434 and 3,647,435, respectively. In a particularly preferred form, such film units are employed in conjunction with a rupturable container, such as, that used above, containing the processing composition having the light-reflecting agent incorporated therein which container is adapted upon application of pressure of distributing its contents to develop the exposed film unit and to provide the light-reflecting layer.

As noted previously, the photographic use of the dyes of the present invention as optical filter agents to prevent post-exposure fogging of a selectively exposed photosensitive material is not limited to diffusion transfer processes nor to such processes employing composite photosensitive elements. While the use of such dyes in composite multicolor diffusion transfer film units is a particularly preferred embodiment of the present invention, these dyes may be used with equally effective results in any photographic process where it is desired to protect a photosensitive material from incident radiation actinic to the photosensitive material within the wavelength range capable of being absorbed by the dye. For example, the subject dyes may be used in conventional tray photographic processing as a component of the processing bath, or they may be present in a layer coextensive with one or both surfaces of a layer of photosensitive material to be processed using conventional tray procedures, provided that they are non-light-absorbing prior to photoexposure and also subsequent to developing the latent image unless the layer containing the dye is to be removed subsequent to processing. In such procedures, the photoexposed photosensitive material will, of course, be transferred from the camera to the processing bath in the absence of radiation actinic to the material.

The subject dyes also may be employed in diffusion transfer processes where the photosensitive and image-receiving elements are separated subsequent to the formation of a transfer image or where a spreader sheet is separated from the photosensitive element to reveal a final image in the negative. In addition to the composite diffusion transfer structures described above, the subject dyes may be used with composite diffusion transfer film units where the final image is to be viewed by transmitted light. Also they may be used in composite film units specifically adapted, for example, for forming a silver transfer image, for developing a negative silver image by monobath processing, for obtaining an additive color image, and for obtaining a dye image by the silver dye bleach process which structures are described in detail in aforementioned copending U.S. Application Ser. No. 101,968, particularly with reference to FIGS. 10 to 13 of the application's drawings.

Although the invention has been discussed in detail throughout employing dye developers, the preferred image-providing materials, it will be readily recognized that other, less preferred, image-providing materials may be substituted in replacement of the preferred dye developers in the practice of the invention. For example, there may be employed dye image-forming materials such as those disclosed in U.S. Pat. Nos. 2,647,049; 2,661,293; 2,698,244; 2,698,798; 2,802,735; 3,148,062; 3,227,550; 3,227,551; 3,227,552; 3,227,554; 3,243,294; 3,330,655; 3,347,671; 3,352,672; 3,364,022; 3,443,939; 3,443,940; 3,443,941; 3,443,943; etc., wherein color diffusion transfer processes are described which employ color coupling techniques comprising, at least in part, reacting one or more color devloping agents and one or more color formers or couplers to provide a dye transfer image to a superposed image-receiving layer and those disclosed in U.S. Pat. Nos. 2,774,668 and 3,087,817, wherein color diffusion transfer processes are described which employ the imagewise differential transfer of complete dyes by the mechanisms therein described to provide a transfer dye image to a contiguous image-receiving layer, and thus including the employment of image-providing materials in whole or in part initially insoluble or nondiffusible as disposed in the film unit which diffuse during processing as a direct or indirect function of exposure.

In view of the foregoing, it will be readily apparent that the subject dyes are useful generally in photographic processes for producing silver, monochromatic and multi-color images using any photosensitive material including conventional and direct positive silver halide emulsions. Depending upon the selected photosensitive material, one or more of the dyes may be used alone or in combination with another optical filter agent, such as another light-absorbing dye, which second dye may be non-color-changing or another pH sensitive dye. If the selected dye or dyes do not possess the desired stability in the processing composition for long term storage therein, they may be initially disposed in the film structure or stored in a double-compartmented pod or in one of two associated pods separate from the processing solution until such time as the pod(s) are ruptured whereupon the dyes are admixed with the processing solution.

Since certain changes may be made in the above product and process without departing from the scope of the invention herein involved, it is intended that all matter contained in the above description or shown in the accompanying drawings shall be interpreted as illustrative and not in a limiting sense.

What is claimed is:

1. An indicator dye of the formula:

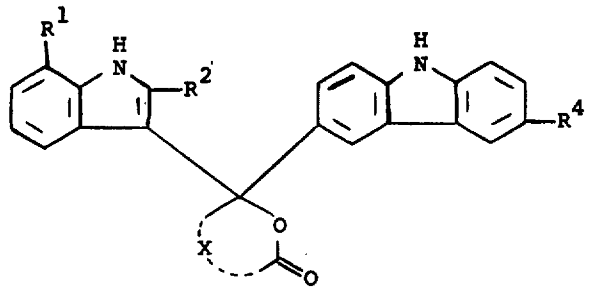

wherein one of $R^1$ and $R^2$ is hydrogen and the other is a hydrogen-bonding group forming a 5-, 6- or 7-membered intramolecular hydrogen-bonded ring with the adjacent —NH— and selected from carboxy, hydroxy, o-hydroxyphenyl, bis trifluoromethyl carbinol, sulfonamido and sulfamoyl; $R^4$ is hydrogen or alkyl containing 1 to 20 carbon atoms; and X represents the carbon atoms necessary to complete a ring-closing moiety selected from phthalide and naphthalide.

2. An indicator dye as defined in claim 1 wherein $R^1$ is a hydrogen-bonding group and $R^2$ is hydrogen.

3. An indicator dye as defined in claim 2 wherein $R^1$ is carboxy.

4. An indicator dye as defined in claim 1 wherein $R^4$ is alkyl.

5. An indicator dye as defined in claim 1 wherein X represents the atoms necessary to complete phthalide.

6. 3-(7-carboxyindol-3-yl)-3-(6-methylcarbazol-3-yl)phthalide.

7. A compound of the formula:

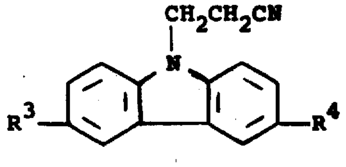

wherein $R^3$ is a group selected from 2-carboxybenzoyl and 8-carboxynaphthoyl and $R^4$ is a group selected from hydrogen and alkyl containing 1 to 20 carbon atoms.

8. A compound as defined in claim 7 wherein $R^4$ is alkyl.

9. A compound as defined in claim 7 wherein $R^3$ is 2-carboxybenzoyl.

10. 3-(2-carboxybenzoyl)-6-methyl-9cyanoethyl-carbazole.

11. A method which comprises the steps of 1. reacting (a) a carbazole of the formula:

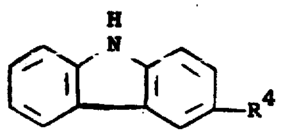

wherein $R^4$ is selected from hydrogen and alkyl containing 1 to 20 carbon atoms and (b) acrylonitrile to form the corresponding 9-cyanoethylcarbazole; and 2. reacting the last-named compound with a reagent selected from phthalic acid, naphthalic acid, phthalic anhydride and naphthalic anhydride in the presence of an acid catalyst to form (c) the corresponding 3-(2-carboxybenzoyl)-9-cyanoethyl carbazole or (d) the corresponding 3-(8-carboxynaphthoyl)-9-cyanoethylcarbazole.

12. A method as defined in claim 11 which includes the step of reacting the compound selected from (c) and (d) with an indole in the presence of acetic anhydride to form the corresponding 3,3-disubstituted phthalide or 3,3-disubstituted naphthalide, said indole having the formula

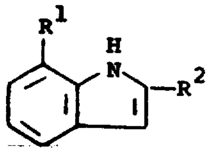

wherein one of $R^1$ and $R^2$ is hydrogen and the other is a hydrogen-bonding group forming a 5-, 6- or 7-membered intramolecular hydrogen-bonded ring with the adjacent —NH— and selected from carboxy, hydroxy, o-hydroxyphenyl, bis trifluoromethyl carbinol, sulfonamido and sulfamoyl.

13. A method as defined in claim 12 which includes the additional step of removing said 9-cyanoethyl group from the reaction product of an indole with said (c) and (d) by treating said reaction product with strong base.

14. A method as defined in claim 11 wherein said $R^4$ of said carbazole (a) is alkyl.

15. A method as defined in claim 11 wherein said reagent is phthalic anhydride.

16. A method as defined in claim 12 wherein said carbazole (a) is 6-methylcarbazole and said reagent is phthalic anhydride.

17. A method as defined in claim 16 wherein said $R^1$ is a hydrogen-bonding group and said $R^2$ is hydrogen.

18. A method as defined in claim 17 wherein said indole is 7-carboxyindole.

19. A method as defined in claim 13 wherein said base is potassium-t-butoxide.

* * * * *